United States Patent

Schreiber et al.

[11] 4,036,886
[45] July 19, 1977

[54] PROCESSES FOR PRODUCING 4- AND 5-PHENYL PENTENALS

[75] Inventors: William Lewis Schreiber, Jackson, N.J.; Gerard Joseph Mosciano, Newton, Pa.; Alan O. Pittet, Atlantic Highlands; Manfred Vock, Locust, both of N.J.; Edward Joseph Shuster, New York, N.Y.

[73] Assignee: International Flavors & Fragrances Inc., New York, N.Y.

[21] Appl. No.: 676,393

[22] Filed: Apr. 12, 1976

Related U.S. Application Data

[60] Continuation-in-part of Ser. No. 507,542, Sept. 19, 1974, which is a division of Ser. No. 283,632, Aug. 25, 1972, Pat. No. 3,862,340.

[51] Int. Cl.$^2$ .................................... C07C 45/00
[52] U.S. Cl. .......................... 260/599; 260/611 A; 260/340.9; 260/340.7; 260/566 R; 252/522; 426/534; 426/536; 426/538
[58] Field of Search .................................... 260/599

[56] References Cited

U.S. PATENT DOCUMENTS 3,365,481  1/1968  Wittig et al. .................... 260/599 X

*Primary Examiner* — Bernard Helfin
*Attorney, Agent, or Firm* — Arthur L. Liberman; Harold Haidt; Franklin D. Wolffe

[57] ABSTRACT

Described are processes for preparing novel 4- and 5-phenyl-pentenals, lower alkyl and lower alkylene acetals thereof having the structure:

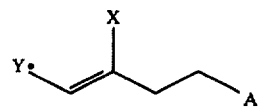

wherein one of X and Y is phenyl and the other of X and Y is hydrogen and A is a moiety selected from the group consisting of:

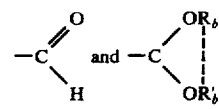

wherein $R_b$ and $R_b'$ separately are the same or different lower alkyl or $R_b$ and $R_b'$ taken together form a lower alkylene group either (i) comprising the step of intimately admixing the lithium salt of a Schiff base of acetaldehyde and an amine with a phenyl-substituted compound selected from the group consisting of phenyl alkanals and phenyl alkenyl bromides in order to produce a phenyl-substituted Schiff base and treating said phenyl-substituted Schiff base with an acid, or (ii) comprising the steps of first admixing phenyl propionaldehyde with a tri-substituted formyl methylene phosphorane in a non-reactive solvent and then heating the resulting mixture.

1 Claim, No Drawings

PROCESSES FOR PRODUCING 4- AND 5-PHENYL PENTENALS

This application is a continuation-in-part of applicants' copending application Ser. No. 507,542, filed on Sept. 19, 1974, which, in turn is a division of applicants' parent application Ser. No. 283,632 filed on Aug. 25, 1972, now U.S. Pat. No. 3,862,340 issued on Jan. 21, 1975.

BACKGROUND OF THE INVENTION

The present invention relates to novel methods for producing certain 4- or 5-phenyl-pentenals, and lower alkyl or lower alkylene acetals, a number of which are novel themselves which are used to alter the flavor and/or aroma of consumable materials. The above-mentioned acetals may also act as precursors for their corresponding free aldehydes which alter the flavor and/or aroma of consumable materials.

There has been considerable work performed relating to substances which can be used to impart flavors and fragrances to various consumable materials. These substances are used to diminish the use requirement of natural materials some of which may be in short supply and to provide such uniform properties in the finished product. Citrus flavors, walnut flavors, chocolate flavors, cinnamon flavors, green vegetable flavors, watermelon flavors, cucumber flavors, green floral aromas, green twiggy aromas, and cinnamon aromas are particularly desirable for many uses in consumable materials.

3-Phenyl-pentenals have been suggested in U.S. patent application Ser. No. 43,555, filed June 4, 1970 now U.S. Pat. No. 3,694,232 for use in cocoa flavors whereby notes characteristic of milk chocolate are provided.

3-Phenyl-4-pentenal is indicated to cause the chocolate beverage to have a fuller, richer sweet milk chocolate flavor. U.S. Pat. No. 3,582,360 issued on June 1, 1971 discloses certain 2-phenyl-2-alkenals as being useful for preparing flavoring compositions and food compositions, particularly those having chocolate or cocoa flavors and/or aroma qualities. Thus, for example, the compound 5-methyl-2-phenyl-2-hexenal is indicated therein to alter imitation cocoa flavor so as to provide a more natural cocoa flavor and impart a character of bitter chocolate.

Acetals are shown to be useful in fragrance formulation at Column 2, lines 50–65 of U.S. Pat. No. 3,636,113. Such acetals have the structures:

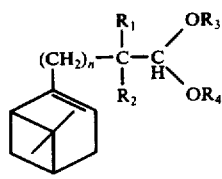

wherein $R_1$ and $R_2$ are either hydrogen or lower alkyl; wherein $R_3$ and $R_4$ are the same or different lower alkyl groups, and wherein $n$ is 1 or 2 and lower alkylene cyclic acetals having the structure

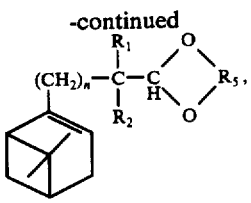

wherein $R_5$ is lower alkylene.

In U.S. patent application Ser. No. 43,555 mentioned above, mention is made of the diethyl acetal of 3-phenyl-4-pentenal and the diethyl acetal of 3-phenyl-3-pentenal; but only as intermediates for producing 3-phenyl-3-pentenal and 3-phenyl-2-pentenal from 3-phenyl-4-pentenal.

In West et al. "Synthetic Perfumes: their Chemistry and Preparation", published by Edward, Arnold & Co., London, England, in 1949, on page 315 cinnamaldehyde dimethyl acetal is stated to "have a fine cinnamon-cassia odor which renders it useful in some Chanel-like fancy perfume and in oriental types like Tabac Blond and Fleur de Tabac". Cinnamaldehyde diethyl acetal is also reported. These materials have the following structures:

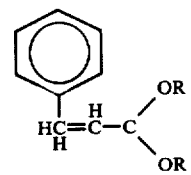

wherein R is methyl or ethyl.

Cinnamaldehyde diethyl acetal is reported in "Perfume and Flavor Chemicals (Aroma Chemicals)" by S. Arctander (published by the author in Montclair, N.J. 11969) as having a "faint but fresh green slightly spicy oily sweet odor and a mild and oily sweet taste." Arctander goes on to state: "since this acetal — like most other acetals — is unstable under mildly acid conditions it finds little if any use in flavor compositions". In addition, Arctander also reports cinnamaldehyde 2,4-dihydroxy-4-methyl-pentane acetal as "soft, tenacious, natural, cinnamon type odor not nearly as harsh as cinnamic aldehyde yet rich and lasting as aldehyde itself". Cinnamic aldehyde dimethyl acetal is also reported by Arctander and with reference to this acetal Arctander states: "It should be noted that pure, aldehyde-free acetal is practically colorless and carries little or no odor similarly to the aldehyde". The ethylene glycol acetal of cinnamic aldehyde is indicated by Arctander to be useful in flavor compositions, such as all spice, cassia, cinnamon, clove and various spice blend and it is stated by Arctander to have a sweet spicy cinnamon all spice taste not quite as sweet as the aldehyde. It should be noted that cinnamic aldehyde ethylene glycol acetal is on the GRAS list and has been given F.E.M.A. No. 2287.

The cinnamic aldehyde acetals of the prior art are not considered to impart certain desired qualities to consumable materials which acetals of 4- and 5-phenyl-pentenals of this invention are capable of doing as more specifically described below.

The prior art cinnamic aldehyde acetal noted above, however, being unsaturated in a position $\alpha,\beta$- to the acetal moiety, are relatively unstable even in aqueous media.

THE INVENTION

It has now been discovered that novel solid and liquid foodstuff and flavoring compositions as well as novel aroma imparting compositions having citrusy, and/or walnut, and/or chocolate, and/or cinnamon, and/or green vegetable, and/or watermelon, and/or cucumber, and/or green floral, and/or green twiggy characteristics found in quality essences and essential oils may be provided by the utilization of certain compounds of the class of 4- and 5-phenyl-pentenals and lower alkyl and lower alkylene acetals thereof.

Furthermore, certain lower alkyl and lower alkylene acetals of the 4- and 5-phenyl-pentenals of this invention will act as precursors in forming the corresponding free aldehydes of this invention. These "precursors" are uniquely useful in that they may be included, preferably, as part of a solid flavor or fragrance imparting composition which is capable of being stored for an indefinite period of time prior to use in a liquid foodstuff or in a perfume formulation or in a cologne. At the point of ultimate use of the flavor or fragrance imparting material, such higher molecular weight acetal is hydrolyzed due to the presence of other acidic constituents and/or an aqueous medium and due to the liquid phase of the material in which it is used.

The term "4- or 5-phenyl-pentenal and lower alkyl and alkylene acetals thereof" as used herein is intended to encompass compounds having the structure:

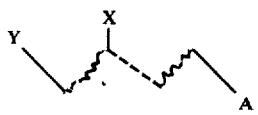

wherein one of X or Y is phenyl and the other of X or Y is hydrogen; wherein one of the wavy or dashed lines is a carbon-carbon double bond and the other two of the wavy or dashed lines is a carbon-carbon single bond; wherein the dashed line is a single bond when X is hydrogen; and wherein A is a moiety selected from the group consisting of

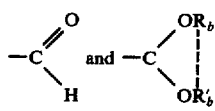

wherein $R_b$ and $R_b'$ separately are the same or different lower alkyl or $R_b$ and $R_b'$ taken together form a lower alkylene group.

Specific examples of compounds falling within the scope of the foregoing structural formula include, without limitation, the following:

5-phenyl-4-pentenal
5-phenyl-2-pentenal
4-phenyl-4-pentenal
4-phenyl-3-pentenal
4-phenyl-2-pentenal
5-phenyl-4-pentenal diethyl acetal
5-phenyl-2-pentenal diethyl acetal
4-phenyl-4-pentenal diethyl acetal
4-phenyl-3-pentenal diethyl acetal
4-phenyl-2-pentenal diethyl acetal
5-phenyl-4-pentenal dimethyl acetal
5-phenyl-2-pentenal dimethyl acetal
4-phenyl-4-pentenal dimethyl acetal
4-phenyl-3-pentenal dimethyl acetal
4-phenyl-2-pentenal dimethyl acetal
5-phenyl-4-pentenal ethylene acetal
5-phenyl-2-pentenal ethylene acetal
4-phenyl-4-pentenal ethylene acetal
4-phenyl-3-pentenal ethylene acetal
4-phenyl-2-pentenal ethylene acetal
5-phenyl-4-pentenal 1,2-propylene acetal
5-phenyl-2-pentenal 1,2-propylene acetal
4-phenyl-4-pentenal 1,2-propylene acetal
4-phenyl-3-pentenal 1,2-propylene acetal
4-phenyl-2-pentenal 1,2-propylene acetal
5-phenyl-4-pentenal methyl ethyl acetal
5-phenyl-2-pentenal methyl ethyl acetal
4-phenyl-4-pentenal methyl ethyl acetal
4-phenyl-3-pentenal methyl ethyl acetal
4-phenyl-2-pentenal methyl ethyl acetal
5-phenyl-4-pentenal di-n-propyl acetal
5-phenyl-2-pentenal di-n-propyl acetal
4-phenyl-4-pentenal di-n-propyl acetal
4-phenyl-3-pentenal di-n-propyl acetal
4-phenyl-2-pentenal di-n-propyl acetal
5-phenyl-4-pentenal di-i-propyl acetal
5-phenyl-2-pentenal di-i-propyl acetal
4-phenyl-4-pentenal di-i-propyl acetal
4-phenyl-3-pentenal di-i-propyl acetal
4-phenyl-2-pentenal di-i-propyl acetal
5-phenyl-4-pentenal di-n-butyl acetal
5-phenyl-2-pentenal di-n-butyl acetal
4-phenyl-4-pentenal di-n-butyl acetal
4-phenyl-3-pentenal di-n-butyl acetal
4-phenyl-2-pentenal di-n-butyl acetal
5-phenyl-4-pentenal 1,3-n-butylene acetal
5-phenyl-2-pentenal 1,3-n-butylene acetal
4-phenyl-4-pentenal 1,3-n-butylene acetal
4-phenyl-3-pentenal 1,3-n-butylene acetal
4-phenyl-2-pentenal 1,3-n-butylene acetal The instant invention furthermore is intended to encompass certain novel compounds included in the above-mentioned list. These novel compounds are broadly defined by the structure:

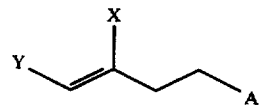

wherein one of X and Y is phenyl and the other of X and Y is hydrogen and A is a moiety selected from the group consisting of

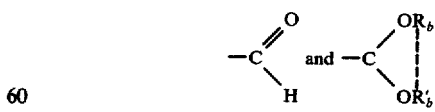

wherein $R_b$ and $R_b'$ separately are the same or different lower alkyl or $R_b$ and $R_b'$ taken together form a lower alkylene group.

Specific examples of these novel compounds are:
5-phenyl-4-pentenal
4-phenyl-4-pentenal
5-phenyl-4-pentenal dimethyl acetal 4-phenyl-4-pentenal dimethyl acetal
5-phenyl-4-pentenal diethyl acetal
4-phenyl-4-pentenal diethyl acetal
5-phenyl-4-pentenal ethylene acetal
4-phenyl-4-pentenal ethylene acetal
5-phenyl-4-pentenal 1,2-n-propylene acetal
4-phenyl-4-pentenal 1,2-n-propylene acetal
5-phenyl-4-pentenal 1,3-n-butylene acetal
4-phenyl-4-pentenal 1,3-n-butylene acetal
5-phenyl-4-pentenal di-n-butyl acetal
4-phenyl-4-pentenal di-n-butyl acetal
5-phenyl-4-pentenal di(2-methyl-1-propyl)acetal
4-phenyl-4-pentenal di(2-methyl-1-propyl)acetal Examples of food flavor and fragrance properties of the 4- and 5-phenyl-pentenals which are preferred in the practice of the instant invention are as follows:

1. 4-Phenyl-4-pentenal:
   Aroma: Green, balsamic fatty; faint woody, nutty, twiggy, citrus cortex; includes a slight green spice-like aromatic nuance.
   Taste: at 0.5 ppm has a fresh walnut kernel pumpkin-seed-like taste. At 2 ppm has an additional watermelon cucumber character. At 10 ppm has a green primary flavor and a metallic, cedar, watermelon rind secondary flavor. Threshold level: 0.1 ppm.

2. 4-Phenyl-2-pentenal:
   Aroma: Has a green, twiggy, cuminic, cortex-like, cinnamon, carvone-like aroma.
   Taste: at 1 and 2 ppm it has a sweet chocolate-like rosy aroma. At 1 ppm has sweet and melon notes. At 2 ppm has a milk chocolate character. At 10 ppm primary flavor is floral and woody and has a secondary cedar flavor. Threshold level: 1 ppm.

3. 5-Phenyl-4-pentenal:
   Taste: At 2 ppm has a fruity, characteristics fresh grapefruit note. At 10 ppm has a green primary flavor and a floral, watermelon, rind secondary flavor. Threshold Level: 1 ppm.
   Aroma: Has a green slight cinnamon note with a natural fattiness.

4. 5-Phenyl-2-pentenal:
   Aroma: Has a green, cutgrass, linseed, cinnamon, sweet aromatic, citrus, lemon and lime-like aroma. At 1 ppm has a light rosy aroma.
   Taste: At 2 ppm has a sweet, cinnamon bark like taste with a grapefruit note. At 10 ppm has a green primary flavor with a floral, watermelon, rind secondary flavor. Threshold level: 1 ppm.

As used herein in regard to flavoring, the term "alter" in its various forms means supplying or imparting a flavor character or note to an otherwise bland, relatively tasteless substance, or augmenting the existing flavor characteristic where a natural flavor is deficient in some regard, or supplementing the existing flavor impression to modify its quality, character or taste.

As used herein the term "foodstuff" includes both solid and liquid ingestible materials which usually do, but need not, have nutritional value. Thus, foodstuffs include meats, gravies, soups, convenience foods, beverages, dairy products, candies, vegetables, cereals, soft drinks, snacks and the like.

The preparation of 5-phenyl-4-pentenal and 4-phenyl-4-pentenal is most preferably carried out by means of reaction of a phenyl allyl bromide (e.g. cinnamyl bromide,

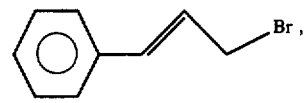

where it is desired to produce 5-phenyl-4-pentenal and α-bromomethyl styrene:

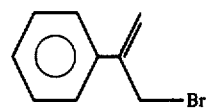

where it is desired to produce 4-phenyl-4-pentenal) with the lithium salt of a Schiff base of acetaldehyde with a primary amine (e.g. a Schiff base of acetaldehyde with cyclohexylamine, or t-butylamine or isopropylamine) thereby forming a 4- or 5-phenyl-4-pentenal Schiff base. This Schiff base is then hydrolyzed thus forming the desired free aldehyde. The free aldehyde may, if desired, then be reacted with a suitable orthoformate and, in addition, a lower alcohol or mixture of different lower alcohols or a lower alkylene glycol or a mixture of lower alkylene glycols or a mixture of lower alcohols and lower alkylene glycols in the presence of an acidic reaction promoter such as paratoluene sulfonic acid, hydrochloric acid or a source therefor such as acetyl chloride, thus forming one or a mixture of lower alkyl acetals and/or lower alkylene glycol acetals which are also useful in our invention. The reaction sequence is generally illustrated as follows:

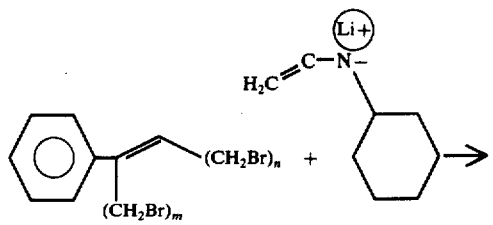

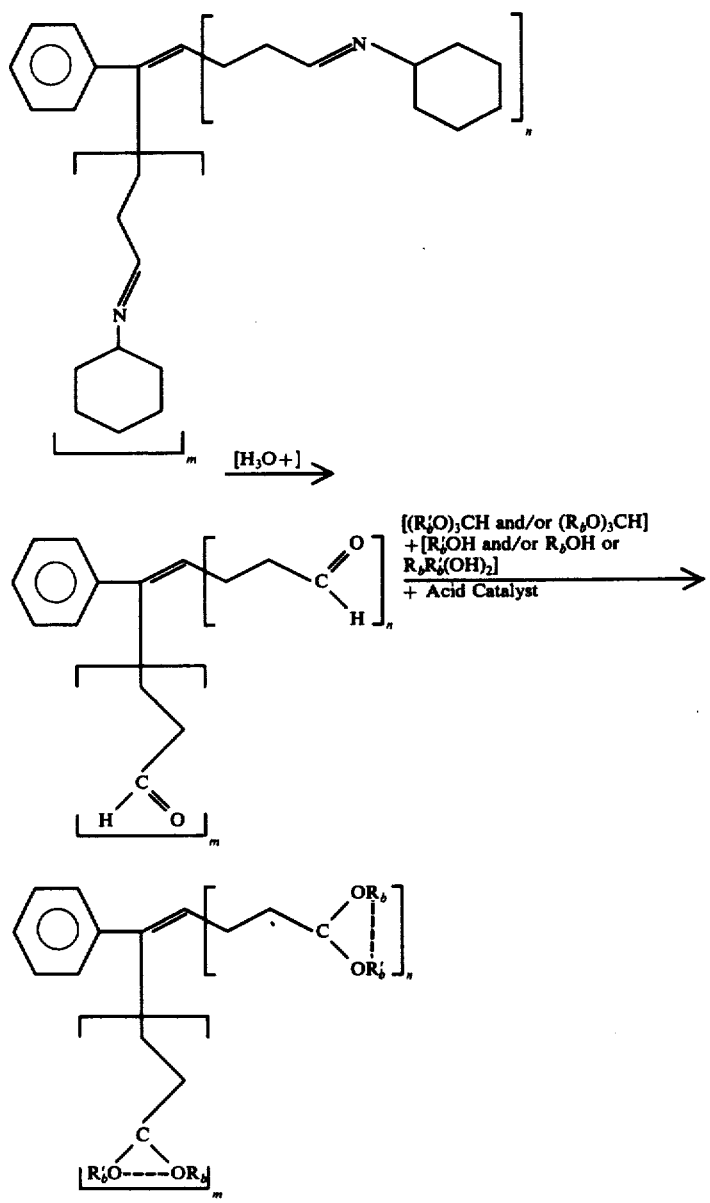

wherein $n$ is zero when $m$ is 1 and $n$ is 1 when $m$ is zero; and wherein $R_b$ and $R_b'$ taken separately are the same or different lower alkyl, e.g. methyl, ethyl, n-propyl, i-propyl, n-butyl, t-butyl or i-butyl and $R_b R_b'$ taken together form a lower alkylene group, e.g. 1,2-ethylene; 1,3-propylene; 1,3-butylene; 1,4- butylene; and 1,2-propylene. A specific illustration of this reaction sequence is as follows:

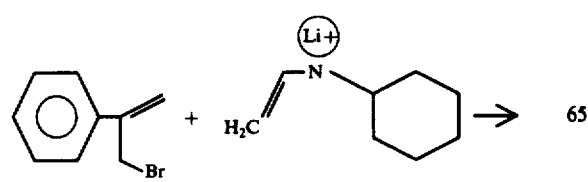

The preparation of the reactant, the lithium salt of the Schiff base of acetaldehyde is carried out by first forming a Schiff base of an amine, such as cyclohexylamine or isopropyl amine with acetaldehyde. An organo lithium compound in a suitable solvent (e.g. n-butyl lithium or phenyl lithium in hexane, diethyl ether benzene or mixtures thereof) is then intimately admixed with an amine such as diisopropyl amine or di(trimethylsilyl) amine to form a lithium amide salt. To the resulting solution at 0° C, the Schiff base is added thereby forming the lithium salt of the Schiff base. The reaction between the lithium salt of the Schiff base thus formed and the phenyl allyl bromide is best carried out in equimolar proportions at temperatures in the range −70° C up to +30° C, the most preferable technique being to allow the reaction mass to warm up from −70° C up to +20° C. The subsequent acidification is preferably carried out at a pH of approximately 1 using, preferably hydrochloric acid or sulfuric acid.

The preparation of 5-phenyl-2-pentenal and, 4-phenyl-2-pentenal and 4-phenyl-3-pentenal may be carried out (1) by means of reaction of a phenyl lower alkanal (e.g. hydrotropaldehyde,

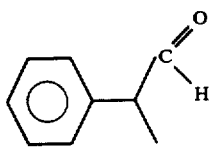

where it is desired to produce 4-phenyl-2-pentenal; phenyl-n-propionaldehyde,

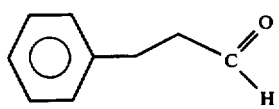

where it is desired to produce 5-phenyl-2-pentenal) with a lithium salt of a Schiff base of acetaldehyde produced according to the conditions set forth above (e.g. a Schiff base of acetaldehyde with cyclohexylamine) thereby forming a phenyl hydroxyl-substituted pentanal Schiff base. This hydroxyl-substituted pentanal Schiff base is then treated with acid thereby forming a phenyl pentenal or a mixture of two phenyl pentenals (since in certain cases, e.g. when producing 4-phenyl-2-pentenal and 4-phenyl-3-pentenal but not when producing 5-phenyl-2-pentenal, when the hydroxyl derivative is dehydrated to isomers with the double bond in two adjacent positions will be formed). (2) If desired, these isomers (when such isomeric mixtures are formed) may be separated by standard separation techniques, e.g. distillation or GLC techniques. (3) The pure isomers or mixtures thereof may, if desired, then be reacted with a suitable orthoformate and in addition a lower alcohol or a mixture of different lower alcohols or a lower alkylene glycol or a mixture of lower alkylene glycols or a mixture of lower alcohols and lower alkylene glycols in the presence of an acidic reaction promoter, such as paratoluene sulfonic acid, hydrochloric acid or a source therefor, such as acetyl chloride one or a mixture of the lower alkyl acetals and/or alkylene glycol acetals useful in our invention. The reaction sequence is generally illustrated as follows:

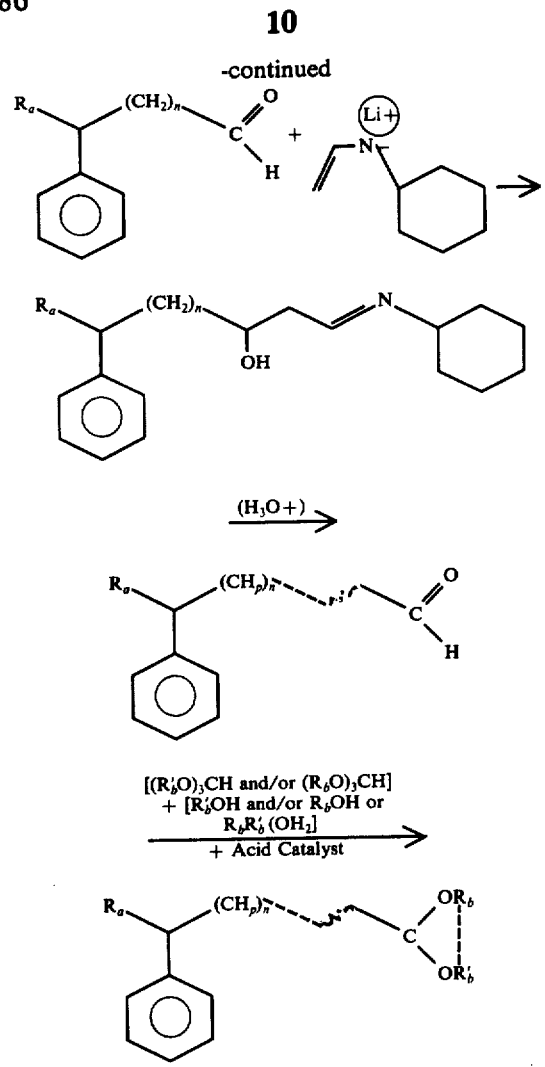

wherein $R_a$ is hydrogen or methyl; $n$ is zero when $R_a$ is methyl; $n$ is 1 when $R_a$ is hydrogen; wherein $p$ is 1 to 2; one of the wavy or dashed lines represents a double bond and the other of the wavy or dashed lines represents a single bond; wherein when $R_a$ is hydrogen the dashed lines is a single bond only; wherein when the dashed line is a double bond $p$ is 1 and when the wavy line is a double bond $p$ is 2; and wherein $R_b$ and $R_b'$ taken separately are the same or different lower alkyl, e.g. methyl, ethyl, propyl, i-propyl, n-butyl, t-butyl, or i-butyl and $R_b$ and $R_b'$ taken together form a lower alkylene group; e.g. 1,2-ethylene; 1,3-propylene; 1,3-butylene; 1,4-butylene and 1,2-propylene. A specific illustration of this reaction sequence is as follows:

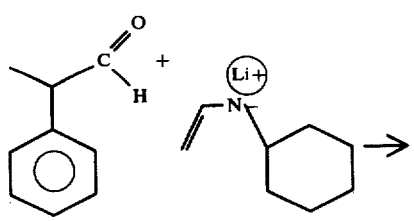

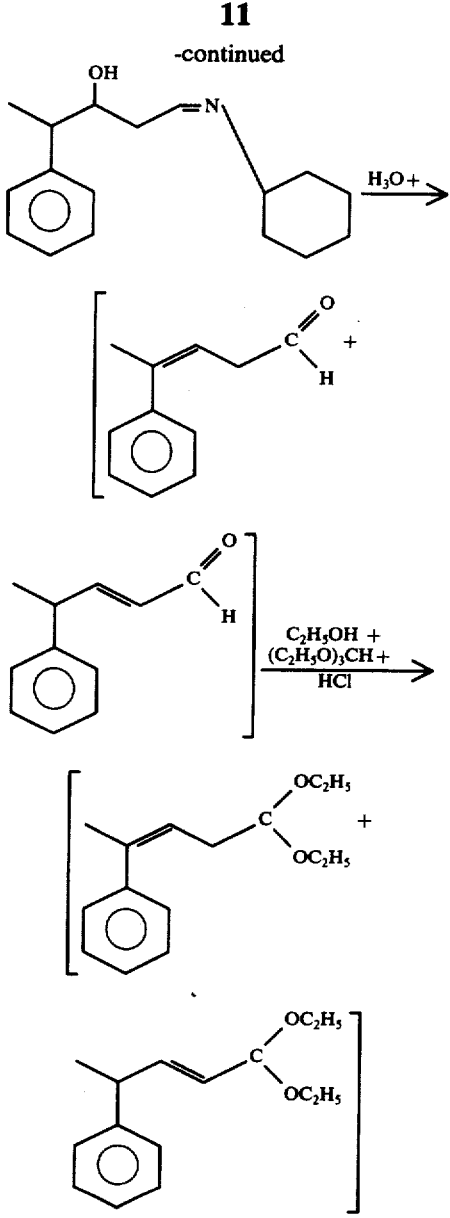

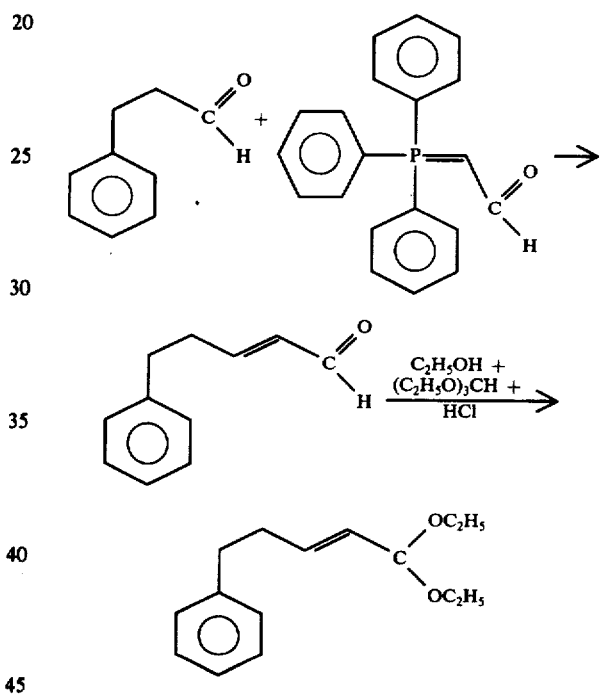

or below reflux conditions preferably and most conveniently at atmospheric pressure. The mole ratio of the two reactants is preferably maintained at 1:1. The reactant concentration in the solvent may vary from 0.1 molar up to 2 molar. (2) The 5-phenyl-2-pentenal may, if desired, then be reacted with a suitable orthoformate and in addition a lower alcohol or a mixture of different lower alcohols or a lower alkylene glycol or a mixture of lower alkylene glycols or a mixture of lower alcohols and lower alkylene glycols in the presence of an acidic reaction promoter, such as paratoluene sulfonic acid, hydrochloric acid or a source therefor such as acetyl chloride, thus forming one or a mixture of the lower alkyl acetals and/or alkylene glycol acetals useful in our invention. The reaction sequence is illustrated as follows:

In the foregoing reaction sequence the initial reaction between the phenyl lower alkanal and the lithium salt of the Schiff base of acetaldehyde is best performed in the presence of a non-reactive solvent, such as benzene or ether at temperatures of the order of −70° C up to +20° C. It is best to mix the reactants at −70° C and allow the reaction mass to slowly warm to room temperature. Furthermore, it is most preferable that the reactants be in equimolar proportion. The concentration of reactants in the solvents can vary from 0.5 molar up to 3 molar. The subsequent acidification which also gives rise to an in situ dehydration is most preferably performed using an aqueous oxalic acid solution and stream distilling the reaction products from the said aqueous oxalic acid solution.

The preparation of 5-phenyl-2-pentenal and its di-lower alkyl acetals and lower alkylene acetals is preferably carried out by (1) first forming the free 5-phenyl-2-pentenal in one step by reacting a tri-substituted formyl methylene phosphorane (e.g. formyl methylene triphenyl phosphorane) with phenyl propionaldehyde. The reaction is carried out in a non-reactive solvent, such as benzene, toluene, xylene, or tetrahydrofuran at When the materials of this invention, the 4- and 5-phenyl-pentenals and the lower alkyl diacetals and lower alkylene acetals of 4- and 5-phenyl-pentenals are used as food flavor adjuvants, the nature of the co-ingredients included with the 4- and 5-phenyl-pentenals and lower dialkyl acetals or lower alkylene acetals thereof in formulating the product composition will, (i.e., as a foodstuff per se or alternatively as a flavoring composition adapted to be added to a foodstuff at some subsequent point of time) serve to alter the organoleptic characteristics of the ultimate foodstuff treated therewith.

Substances suitable for use herein as co-ingredients or flavoring adjuvants are well known in the art for such use being extensively described in the relevant literature. Apart from the requirement that any such material be "ingestibly" acceptable, and thus non-toxic or otherwise non-deleterious, nothing particularly critical resides in the selection thereof. Accordingly, such materials, which may in general be characterized as flavoring adjuvants or vehicles comprise broadly, stabilizers, thickeners, surface active agents, conditioners, flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3 tertiary butyl-4-hydroxyanisole), butylated hydroxy toluene (2,6-di-tertiary-butyl-4-methyl phenol), propyl gallate and the like, sequestrants, e.g., citric acid.

Thickener compounds include carriers, binders, protective colloids, suspending agents, emulsifiers and the like, e.g., agar-agar; carrageenan; cellulose and cellulose derivatives such as carboxymethyl cellulose and methyl cellulose; natural and synthetic gums such as gum arabic, gun tragacanth; gelatin, proteinaceous materials; lipids; carbohydrates; starches pectins, and emulsifiers, e.g., mono- and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers; anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Flavorants and flavor intensifiers include organic acids, e.g., fatty saturated acids, unsaturated acids and amino acids; alcohols, e.g., primary and secondary alcohols; esters, carbonyl compounds including aldehydes and ketones as well as lactones; cyclic organic materials including benzene derivatives; isocyclics; heterocyclics such as furans, particularly pyridines, pyrazines (particularly monoalkyl, dialkyl, trialkyl and tetraalkyl substituted pyrazines) and the like, sulfur-containing materials including thiazoles, disulfides, thiols, sulfides, aldehydes, (for example, 3-phenyl-4-pentenal, 3-phenyl-3-pentenal, 3-phenyl-2-pentenal, 2-phenyl-2-pentenal, and 2-phenyl-3-methyl-2-butenal; disulfides and the like; so-called flavor potentiators such as monosodium glutamate, guanylates, inosinates, natural and synthetic flavorants such as vanillin, ethyl vanillin, diacetyl, phenethyl 2-furoate, maltol, natural gums and the like; spices, herbs, essential oils and extractives including "bitterness principles" such as theobromin, caffein, naringin and other suitable materials creating a bitter effect.

The specific flavoring adjuvant selected for use may be either solid or liquid, depending upon the desired physical form of the ultimate product, i.e., foodstuff, whether simulated or natural, and should, in any event, be capable of providing an environment in which the 4- or 5-phenyl-pentenals or dilower alkyl acetals or lower alkylene acetals thereof can be dispersed or admixed to provide a homogeneous medium. In addition, selection of one or more flavoring adjuvants as well as the quantities thereof will depend upon the precise organoleptic character desired in the finished product; thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of 4- or 5-phenyl-pentenal or di-lower alkyl acetal or lower alkylene acetal thereof employed in a particular instance can vary over a relatively wide range whereby to achieve desired organoleptic effects having reference to the nature of the product. All parts and percentages given herein are by weight unless otherwise specified. Thus, correspondingly greater amounts would be necessary in those instances wherein the ultimate food composition to be flavored is relatively bland to the taste, whereas relatively minor quantities may suffice for purposes of enhancing a composition merely deficient in natural flavor or aroma. Thus, the primary requirement is that the amount selected to be effective, i.e., sufficient to alter the organoleptic characteristics of the parent composition, whether foodstuff per se or flavoring composition. Thus, the use of insufficient quantities of the 4- or 5-phenyl-pentenal or di-lower alkyl acetal or lower alkylene acetal thereof will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of 4- or 5-phenyl-pentenal or di-lower alkyl acetal or lower alkylene acetal thereof ranging from a small but effective amount, e.g., 0.1 part per million up to about 20 part per million by weight based on total compositions are suitable. Concentrations in excess of the maximum quantities stated are not normally recommended since they fail to provide commensurate enhancement of organoleptic properties. In those instances wherein the 4- or 5-phenyl-pentenal or di-lower alkyl acetal or lower alkylene acetal thereof is added to the foodstuff as an integral component of a flavoring composition, it is, of course, essential that the total quantity of flavoring composition employed be sufficient to yield an effective 4- or 5-phenyl-pentenal (or di-lower alkyl acetal or lower alkylene acetal thereof) concentration in the foodstuff product.

Food flavoring compositions prepared in accordance with the present invention preferably contain the 4- or 5-phenyl-pentenal or di-lower alkyl acetal or lower alkylene acetal thereof in concentrations ranging from about 0.4% up to 20% by weight, based on the total weight of said flavoring composition.

The compositions described herein can be prepared according to conventional techniques well known in the art for such purposes. Thus, liquid products as typified by cake batters, egg nog and chocolate milk can be formulated by merely admixing the involved ingredients within the proportions stated in a suitable blender to obtain the desired consistency, homogeneity of dispersion, etc. Alternatively, flavoring compositions in the form of particulate solids can be conveniently prepared by admixing the 4- or 5-phenyl-pentenal or di-lower alkyl acetal or lower alkylene acetal thereof with, for example, gum arabic, gum tragacanth, carrageenan and the like, and thereafter, spray-drying the resultant mixture whereby to obtain the particulate solid product. Pre-prepared flavor mixes in powder form e.g., cocoa mix may be obtained by mixing the dried solid components e.g., milk solids, sugar and the like and 4- or 5-phenyl-pentenal or di-lower alkyl acetal or lower alkylene acetal thereof in a dry blender until the requisite degree of uniformity is achieved.

It is presently preferred to combine with the 4- or 5-phenyl-pentenal or di-lower alkyl acetal or lower alkylene acetal thereof the following flavoring adjuvants: vanillin, heliotropine, amyl isovalerate, butyl isovalerate, methyl cyclopentenolone, citral, amyl alcohol, ethyl alcohol, phenyl ethyl acetate, di-acetyl, isoamylalcohol furfural, phenyl acetic acid, isovaleraldehyde, phenyl ethyl alcochol and maltol and mixtures thereof.

The compounds of our invention have been found to be useful in perfumery where twiggy, cuminic, citrus, green, cutgrass, linseed or cinnamon notes are desired. The 4- or 5-phenyl-pentenals or di-lower alkyl acetals or lower alkylene acetals thereof of this invention and an auxiliary perfume ingredient, including, for example, alcohols, aldehydes, nitriles, esters, cyclic ethers, and natural essential oils, may be admixed so that the combined odors of the individual components product a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by utilizing or moderating the olfactory reaction contributed by another ingredient in the composition.

The amount of the acetal compound of this invention which will be effective in perfume compositions depends in many factors, including the other ingredients, their amounts and the effects which are desired. It has been found that perfume compositions containing as little as 1% of the compounds of this invention or even less, can be used to impart a scent odor to soaps, cosmetics, and the other products. The amount employed can range up to 20% of the fragrance components and will depend on considerations of cost, nature of the end product, the effect desired on the finished product and the particular fragrance sought.

The 4- and 5-phenyl-pentenals or di-lower alkyl acetals and lower alkylene acetals thereof of this invention are useful in a perfume composition as an olfactory component in detergents and soaps; space odorants and deodorants; perfumes; colognes; toilet waters; bath preparations, such as bath oils and bath solids; hair preparations, such as lacquers, brilliantines, pomades and shampoo; cosmetic preparations, such as creams, deodorants, hand lotions, and sun screens; powders, such as talcs, dusting powders, face powders and the like. When used as an olfactory component of a perfumed article, as little as 100 ppm of one or more of the preferred acetals of this invention will suffice to impart either a green, balsamic, cinnamic-like character to the topnote of the fragrance employed or a green, rosy character to the topnote of the fragrance employed or a green, rosy note to the body of the fragrance employed. Generally, no more than 0.5% of the compounds of this invention based on the ultimate end product is required in the perfume composition.

In addition, the perfume composition or fragrance composition of this invention can contain a vehicle or carrier for the acetals alone or with other ingredients. The vehicle can be a liquid such as an alcohol, non-toxic alochol, non-toxic glycol, or the like. The carrier can also be an absorbent solid, such as a gum (e.g. gum arabic) or components for encapsulating the composition (such as gelatin).

It will thus be apparent that the acetals according to the present invention can be utilized to alter the sensory property, particularly organoleptic properties, such as flavor and/or fragrance of a wide variety of consumable materials.

The following Examples are given to illustrate embodiments of the invention as it is presently preferred to practice it. It will be understood that these Examples are illustrative, and the invention is not to be considered as restricted thereto except as indicated in the appended claims.

EXAMPLE I

PREPARATION OF 4-PHENYL-4-PENTENAL 3.50 grams of di(trimethylsilyl)amine is dissolved in 15 ml diethyl ether and stirred at 0° C as 12.5 ml of 1.6 N n-butyl lithium in hexane is added by syringe at 0° C. 2.50 Grams of the Schiff base of acetaldehyde with cyclohexylamine is added. The resulting mixture is then cooled to −70° C and 4.0 grams of α-bromomethyl styrene is added. The reaction mass is then allowed to warm to room temperature and is maintained at approximately 10° C for a period of 12 hours. 10 ml of water is then added to the reaction mass followed by approximately 4 ml of concentrated hydrochloric acid whereby the pH of the reaction mass is 1.

The resulting mixture was extracted with diethyl ether and the product was isolated as follows: The ether solution was stirred with an aqueous solution containing 1.5 grams of Girard's reagent "P" (carboxymethylpyridinium chloride hydrazide) and 1 ml acetic acid. After approximately one hour, the organic phase was separated from the aqueous phase and the aqueous phase is extracted twice with diethyl ether. The aqueous phase is then treated with 2 ml. concentrated hydrochloric acid and stirred with diethyl ether for approximately 4 hours. The resulting mixture separates into two phases and the phases are separated. The diethyl ether layer is washed with water and saturated sodium bicarbonate and then dried over anhydrous sodium sulfate and evaporated to give 0.5 gram of a light yellow oil which is 98–99% pure (as determined by GLC). NMR, mass spectral and IR analysis yield the information that the resulting product is 4-phenyl-4-pentenal. The NMR analysis is as follows:

| ppm | Interpretation | |
|---|---|---|
| 9.76 | HC=O— (s) | 1H |
| 7.31 | Aromatic protons | 5H |
| 5.08 | Ar—C | 2H |
| 5.30 | ‖ | |
| | C | |
| | ╱ ╲ | |
| | H   H | |
| 2.68 | =C —CH$_2$ + | 4H |
| | —CH$_3$ — C = O | |

EXAMPLE II

PREPARATION OF 5-PHENYL-2-PENTENAL 1.34 grams (0.01 mole) of 3-phenyl propionaldehyde is dissolved in 10 ml of benzene along with 3.25 grams of formyl methylene triphenyl phosphorane. The resulting mixture is refluxed for a period of 15 hours. The solvent is then evaporated from the reaction mass and the resulting residue is extracted several times with isopentane. The solvent is then evaporated yielding 0.90 grams of a yellow oil consisting of 85% 5-phenyl-2-pentenal confirmed by IR, NMR, GLC and mass spectral analysis. The NMR analysis of 5-phenyl-2-pentenal is as follows:

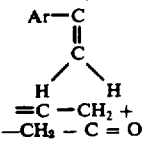

EXAMPLE III

PREPARATION OF 4-PHENYL-2-PENTENAL AND 4-PHENYL-3-PENTENAL 2.20 grams of diisopropylamine in 2.5 ml ether is admixed with 9.0 ml of 2.3N phenyl lithium (in a solvent containing 70 parts of benzene and 30 parts of diethyl ether) and the resulting mixture is stirred at 0° C for a period of 15 minutes. 2.60 Grams of the cyclohexylimine of acetaldehyde is added at 0° C and the resulting mixture is stirred for a period of 30 minutes. The mixture is then cooled using a dry ice bath to −70° C and 2.68 gms of hydrotropic aldehyde is added thereto. The mixture is then allowed to warm gradually and kept at room temperature for a period of approximately 15 hours. Water is added to the reaction mass at this point and the mixture is stirred for a period of 15 minutes. The two resulting liquid phases are then separated and the organic phase is evaporated. The resulting organic residue is then steam distilled from aqueous oxalic acid (15 grams in 150 ml. water) yielding 250 ml. distillate. The distillate is then extracted with diethyl ether and the ether extract is washed using aqueous sodium bicarbonate, and dried over anhydrous sodium sulfate and evaporated yielding 2.10 grams of a yellow oil which is a mixture of 4-phenyl-2-pentenal and 4-phenyl-3-pentenal. Each of the 4-phenyl-2-pentenal and 4-phenyl-3-pentenal is separated using gas liquid chromatography and identified using IR, NMR and GLC techniques.

The NMR spectrum of 4-phenyl-2-pentenal is as follows:

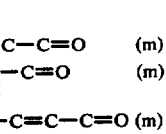

EXAMPLE IV

PREPARATION OF 5-PHENYL-4-PENTENAL 1.20 grams of diisopropyl amine is dissolved in 20 ml diethyl ether and stirred at 0° C as 4.4 ml of 2.3N phenyl lithium is added by syringe. After several minutes, 1.30 grams of the imine of cyclohexylamine with acetaldehyde is added. After 15 minutes at 0° C the mixture is cooled using a dry ice bath to −70° C and 2.00 grams of cinnamyl bromide is added. The reaction mass is then allowed to warm to room temperature and maintained at approximately 20° C for a period of 5 hours. Water is then added to the reaction mass followed by 10% sulfuric acid in order that the pH of the reaction mass is approximately 1. The mixture is then stirred for approximately 15 minutes and the organic phase is separated and washed with water and then saturated sodium bicarbonate. The organic layer is then evaporated and the resulting residue is stirred with 3.0 grams of Girard reagent P (carboxymethylpyridinium chloride hydrazide) in water with 1 ml of acetic acid. After approximately one half hour the resulting aqueous layer is extracted several times with diethyl ether. The ether extract is discarded and the aqueous layer is then treated with 3 ml of concentrated hydrochloric acid and then extracted with diethyl ether. The diethyl ether layer is then washed with water, saturated sodium bicarbonate solution, dried over anhydrous sodium sulfate and evaporated to yield 0.64 grams of a yellow oil having a purity of 99.5% IR, NMR and mass spectral analysis yield information that the product is 5-phenyl-4-pentenal. The NMR analysis of 5-phenyl-4-pentenal is as follows:

| ppm | Interpretation | | |
|---|---|---|---|
| 9.76 | HC=O | (s) | 1H |
| 7.26 | Aromatic protons | (m) | 5H |
| 6.50–6.00 | Olefinic protons | (m) | 2H |
| 2.54 | =C—CH$_2$ + CH$_2$—C=O | | 4H |

EXAMPLE V

Narcisse Fragrance Formulation

The following mixture is prepared:

| Ingredients | Parts |
|---|---|
| Phenyl ethyl phenyl acetate | 15 |
| 4-Phenyl-4-pentenal | 10 |
| 4-Phenyl-2-pentenal | 5 |
| Heliotropine | 20 |
| Paracresyl phenyl acetate | 5 |
| Acetyl isoeugenol | 10 |
| Benzyl acetate | 3 |
| Ylang | 2 |

| Ingredients | Parts |
|---|---|
| Isoeugenol | 5 |
| Paracresol | 1 |
| Nerol coeur | 15 |
| Phenyl ethyl alcohol | 20 |
| Terpineol | 20 |
| Geraniol coeur | 20 |
| Linalool | 25 |
| Benzyl alcohol | 50 |

The 4-phenyl-4-pentenal imparts a twiggy cortex lemony note thereby improving the above narcisse formulation. The 4-phenyl-2-pentenal imparts a green, styrallyl, cuminic note to the narcisse formulation.

EXAMPLE VI

New Mown Hay Perfume Formulation

The following formulation is prepared:

| Ingredients | Parts |
|---|---|
| Honey base | 25 |
| Lavandin | 60 |
| Hawthone | 20 |
| Acetanisol | 5 |
| n-Butyl quinoline | 3 |
| Anisic aldehyde | 15 |
| Chamomile | 1 |
| Mate absolute 50% | 5 |
| Coumarin | 10 |
| 5-Phenyl-2-pentenal | 10 |
| 5-Phenyl-4-pentenal | 5 |

The 5-phenyl-2-pentenal imparts to the above formulation a cutgrass, cinnamon note. The 5-phenyl-4-pentenal imparts to this formulation a natural, fatty, green undertone.

EXAMPLE VII

Grapefruit Flavor

The following formulation is prepared:

| Ingredient | Parts |
|---|---|
| Grapefruit oil | 92 |
| Bergamot oil | 2 |
| Citral | 3 |
| Amyl alcohol | 1 |
| Ethyl acetate | 1 |
| 5-Phenyl-4-pentenal diethyl acetal | 1 |
| Ethyl alcohol | 900 |
| | 1000 |

When the above grapefruit formulation is added to sucrose-sweetened, non-flavored, carbonated beverages at the rate of 0.1%, an excellent grapefruit drink is prepared. The 5-phenyl-4-pentenal diethyl acetal gives a fruitier peeliness to the above formulation thereby making it more desirable than the formulation without said 5-phenyl-4-pentenal diethyl acetal. This effect rendered by the 5-phenyl-4-pentenal diethyl acetal can also be achieved by using 0.5 parts of 5-phenyl-2-pentenal diethyl acetal in the above formulation.

EXAMPLE VIII

Cocoa Flavor

The following formulation is prepared:

| Ingredients | Parts |
|---|---|
| Dimethyl sulfide | 0.2 |
| Phenyl ethyl acetate | 0.6 |
| Diacetyl (10% in propylene glycol) | 0.2 |
| Isoamyl alcohol | 0.1 |
| Furfural (50% in propylene glycol) | 0.2 |
| Phenyl acetic acid | 12.0 |
| 4-Phenyl-4-pentenal ethylene glycol acetal | 20.0 |
| Isovaleraldehyde | 38.0 |
| Phenyl ethyl alcohol | 3.0 |
| Benzaldehyde | 1.0 |
| Maltol | 20.0 |
| Venillin | 60.0 |
| Ethyl alcohol | 844.7 |

The 4-phenyl-4-pentenal propylene glycol acetal improves the cocoa-like note in this otherwise bland chocolate flavor formulation which does not contain said acetal. The 4-phenyl-4-pentenal ethylene glycol acetal can be replaced by 60 parts of 4-phenyl-4-pentenal diethyl acetal and the same effect will be imparted to the overall formulation.

EXAMPLE IX

Basic Walnut Formulation

The following formulation is prepared:

| Ingredients | Parts |
|---|---|
| Vanillin | 5.0 |
| Heliotropine | 5.0 |
| Sage Clary French | 0.1 |
| Patchouli Oil 1% (in 95% ethanol) | 0.2 |
| Benzaldehyde | 0.6 |
| Methyl cyclopentenolone | 9.0 |
| Methyl cyclopentenolone valerate | 5.0 |
| Amyl isovalerate | 10.0 |
| Butyl isovalerate | 7.0 |
| Propylene glycol | 150.0 |
| Foenugreek, solid extract (10% in propylene glycol/water (1:1)) | 800.0 |

The addition of 4-phenyl-4-pentenal diisopropyl acetal at the rate of 5% to the basic formulation adds a note as found in fresh walnut kernels, improving the natural character of this flavor. Both the flavor with the 4-phenyl-4-pentenal diisopropyl acetal and without the 4-phenyl-4-pentenal diisopropyl acetal were compared at the rate of 20 ppm in water.

What is claimed is:

1. The process of preparing a phenyl pentenal selected from the group consisting of 5-phenyl-4-pentenal and 4-phenyl-4-pentenal comprising the steps of (i) reacting a phenyl alkenyl bromide selected from the group consisting of phenyl allyl bromide having the structure:

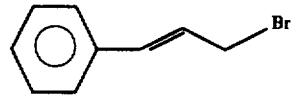

and α-bromomethyl styrene having the structure:

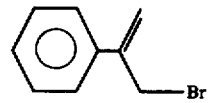

with the lithium salt of a Schiff base of acetaldehyde with an organic amine thereby forming a 4- or 5-phenyl-4-pentenal Schiff base, the temperature range of the reaction between the phenyl alkenyl bromide and the Schiff base being from −70° C up to +30° C, and (ii) subsequently acidifying the resultant 4- or 5-phenyl-4-pentenal Schiff base at a pH of approximately 1 with an acid selected from the group consisting of hydrochloric acid and sulfuric acid.

* * * * *